US007871581B1

(12) United States Patent
Coleman et al.

(10) Patent No.: US 7,871,581 B1
(45) Date of Patent: Jan. 18, 2011

(54) MEDICAL INSTRUMENT HOLDING ASSEMBLY AND METHOD FOR IMPROVED PRE-STERILIZATION CLEANING USING SAME

(75) Inventors: Billy Donald Coleman, Chandler, AZ (US); John Forrest May, Tucson, AZ (US)

(73) Assignee: Patient Care Solutions, LLC, Las Vegas, NV (US)

( * ) Notice: Subject to any disclaimer, the term of this patent is extended or adjusted under 35 U.S.C. 154(b) by 845 days.

(21) Appl. No.: 11/550,924

(22) Filed: Oct. 19, 2006

(51) Int. Cl.
*A61L 2/00* (2006.01)
*A61L 15/00* (2006.01)
*A47H 13/00* (2006.01)
*A47F 7/00* (2006.01)
*B65D 81/24* (2006.01)
*B65D 83/10* (2006.01)

(52) U.S. Cl. .................... 422/300; 211/120; 211/85.13; 206/210; 206/363; 206/438

(58) Field of Classification Search ................. 422/300; 211/120, 85.13; 206/210, 438, 363
See application file for complete search history.

(56) References Cited

U.S. PATENT DOCUMENTS

| 3,925,014 | A | * | 12/1975 | Langdon | 422/310 |
| 4,229,420 | A | * | 10/1980 | Smith et al. | 422/310 |
| 4,577,755 | A | * | 3/1986 | Ramsay | 206/370 |
| 5,137,151 | A | * | 8/1992 | Choate | 206/370 |
| 5,843,388 | A | * | 12/1998 | Arroyo et al. | 422/300 |
| 6,759,017 | B2 | * | 7/2004 | Wu et al. | 422/300 |

* cited by examiner

*Primary Examiner*—Sean E Conley
*Assistant Examiner*—Kevin C Joyner
(74) *Attorney, Agent, or Firm*—Jeffrey D. Moy; Weiss & Moy, P.C.

(57) ABSTRACT

A medical instrument holding assembly for improved pre-sterilization cleaning with or without lubrication of the instruments is provided. The medical instrument holding assembly includes a coil or a series of plates defining instrument receiving gaps, opposing support ends, a perforated retracting member that maintains the instruments in an open position so that cleaning can reach the hard to reach areas of the instrument, and restraint bands for holding the instruments in the medical instrument holding assembly during handling. The method is also included for improved pre-sterilization cleaning using the medical instrument holding assembly.

12 Claims, 8 Drawing Sheets

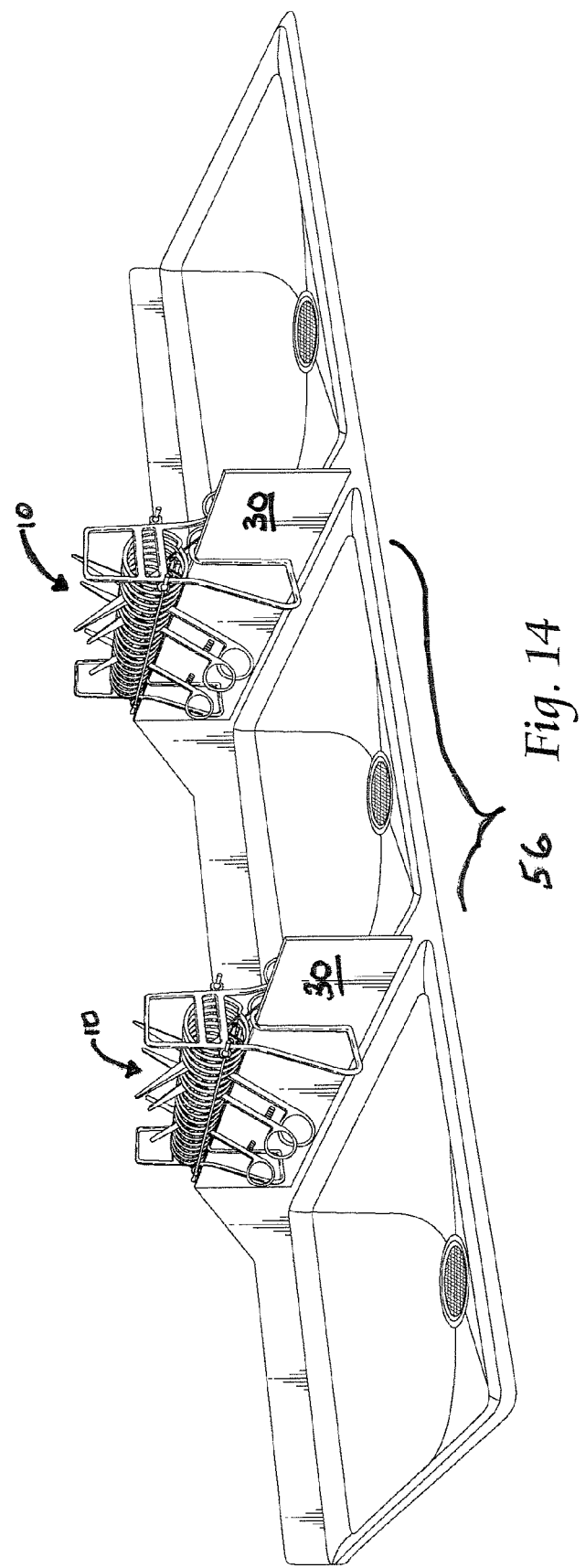

MEDICAL INSTRUMENT HOLDING ASSEMBLY AND METHOD FOR IMPROVED PRE-STERILIZATION CLEANING USING SAME

FIELD OF THE INVENTION

This invention relates generally to the cleaning of medical instruments. More specifically, this invention relates to a surgical instrument holding assembly and method for improved pre-sterilization cleaning of the surgical instruments.

BACKGROUND OF THE INVENTION

Infection control is of serious concern in hospitals, laboratories and other health care facilities. The prevention of health risks to staff and patients is of the highest priority. Contaminated instruments, especially surgical instruments, can be a source of infection transmission and cross contamination. The most common types of contaminants found on instruments are blood, body fluids, tissue and surgical residue, soil, bacterial and viral mass. The most stubborn contaminant on surgical instruments and the one which is the hardest to remove is normally coagulated blood. As defined in ANSI/AAMI ST35 (1996), "contaminated" means the state of having been actually or potentially in contact with microorganisms. As used in health care, the term generally refers to microorganisms that might be capable of producing disease or infection. As also defined therein, "decontamination" is defined as follows: "[T]he use of physical or chemical means to remove, inactive, or destroy bloodborne pathogens on a surface or item to the point where they are no longer capable of transmitting infectious particles and the surface or item is rendered safe for handling, use or disposal" [29 CFR 1910.1030]. The term is generally used in health care facilities with reference to all pathogenic organisms, not just those transmitted by blood.

In addition to causing infection and cross contamination, these contaminants also cause pitting, staining, and corrosion of the instruments if the contaminants are left on the instruments for any extended period of time, especially if the contaminant residues are allowed to dry. The most damaging procedure is to allow dried-on residues to become baked-on stains in the sterilization autoclave. The temperature of the autoclave (250°-270°) will cause chemical reactions that can make the stain permanent. Therefore, thorough pre-sterilization washing of the contaminated instruments shortly after surgery is the best defense against cross contamination and instrument corrosion, pitting, and staining caused by such contaminant residues.

Instruments are a major asset and represent a significant investment by a hospital, health care provider or laboratory. In addition, medical professionals want to ensure the utmost quality and integrity of their surgical instruments at all times and therefore damaged instruments are unacceptable. The cost of replacing surgical instruments is far greater than the cost of maintaining them by proper cleaning and maintenance. Considering that surgical instrument trays for major surgeries can bear price tags of $20,000 or more and that individual instruments can cost several hundred dollars each, sterile processing (SP) technicians must be well versed in the care and handling of surgical instruments and must engage in preventive maintenance. A properly cleaned and reprocessed instrument is to a surgeon what a chisel and hammer is to a sculptor: a set of tools worthy of respect and critical to the outcome of the professional's surgical or creative endeavor.

Contaminated surgical instruments are typically processed as follows: First, there is a cleaning (or pre-disinfection) by substantially eliminating the contaminants by efficient cleaning and bio-cleansing. Next, the instruments are disinfected followed by sterilization in an autoclave. To ensure sterile integrity, the instruments are then stored in sterile conditions. Therefore, the cleaning step is the linchpin of an effective disinfection and sterilization process. If the instruments are not clean, they cannot be sanitized, disinfected or sterilized with any certainty. An autoclave does not clean; it will only sterilize.

Cleaning may be performed manually, mechanically, or by using a combination of both methods. Recommendations suggest that a three deep sink configuration be used for manual cleaning. The first sink is the wash sink which contains the cleaning solution. The second sink is typically the rinse sink designed to remove any detergent or remaining residue. A third sink may be needed for the final rinse with distilled or deionized water to prevent spotting on the instrumentation.

Automated mechanical pre-sterilization cleaning by washer sanitizers has become the choice of most hospitals, health care providers and laboratory practitioners. Washer sanitizers for medical and laboratory purposes have a rinse and washing cycle for removing contaminants with the use of detergents or the like. The washer sanitizers typically include one or more racks designed to hold instrument trays (also known as "decontamination pans"). The washer sanitizer mechanically cleans instruments by a spray action known as impingement from sprayers (not shown) inside the washer sanitizer. Impingement is the water force making contact with the instrument. Each type of impingement system also requires a specialized detergent formulation.

Ultrasonic cleaners are another type of mechanical washer, designed for fine cleaning of medical devices to remove contaminants from hard to reach areas like crevices, joints, grooves, hinges, box locks, etc. Gross contaminants must be removed from instruments before processing in the ultrasonic cleaner because heavy contamination can inhibit the cleaning activity.

In the past, contaminated instruments have been haphazardly laid at the bottom of the instrument trays after opening the instruments to expose the hard to reach areas to the cleaning process. The instrument trays are then put on the one or more racks in the washer sanitizer. Attempts to improve this cleaning process have included the use of instrument string members and other devices. Instrument String members have been used to hold the instruments open in the instrument tray with the instruments stacked horizontally on top of one another.

Unfortunately, these practices (including open contaminated instruments on the bottom of the instrument tray, strung onto instrument string members, etc.) have not provided sufficient cleaning, especially for the hard to reach areas of surgical instruments. In addition, these practices also subject the instruments to a risk of damage as they contact each other during the cleaning process. The instruments may also fall off of the instrument string members during the cleaning process.

In addition to pre-sterilization cleaning, instruments should be lubricated regularly after cleaning and before autoclaving as part of a maintenance regimen. Proper lubrication keeps instruments from rubbing and scraping, thus preventing dulling and strain to joints and hinges. Lubricants may be applied during mechanical processing cycles, such as within the washer-sanitizer.

There is therefore for an instrument holding assembly and method that substantially increase the efficiency of pre-sterilization cleaning to substantially minimize infection rates and cross contamination. There is another need for an assembly and method that substantially permit proper positioning of the instruments and better exposure of the hard to reach instrument areas for optimal cleaning and lubrication. There is an additional need for an assembly and method that substantially prevent instrument damage from contaminant residues and during cleaning thus protecting the value of the instrument and lessening repairs and replacement thereof thus substantially reducing the overall instrument inventory. The present invention fulfills these needs and provides other related advantages.

SUMMARY OF THE INVENTION

The present invention resides in an instrument holding assembly for holding contaminated surgical instruments during pre-sterilization cleaning with or without lubrication, which provides for better cleaning, especially of the hard to reach areas of instruments, while being protective of the instruments.

The medical instrument holding assembly comprises, generally, segregation means defining instrument-receiving gaps, and perforated retractor means extending through the segregation means for holding one or more medical instruments in an open position in said instrument-receiving gaps. The medical instrument holding assembly may further include restraint means adapted to restrain the one or more medical instruments in said instrument-receiving gaps.

In a first embodiment, the medical instrument holding assembly comprises, generally, a coil defining adjacent medical instrument-receiving gaps, opposing support ends for the coil, a perforated retractor member adapted to maintain one or more medical instruments in an open position in said medical instrument-receiving gaps, and a pair of restraints adapted to restrain the one or more medical instruments therein. The medical instrument holding assembly may further comprise a stabilizing rod for stabilizing the assembly. The coil segregates the instruments from one another.

The medical instrument holding assembly may be loaded with contaminated medical instruments and configured for removable placement in an instrument tray for use in a washer sanitizer. The medical instrument holding assembly may also be used on sink dividers or on other surfaces.

The coil may be a straight cylindrical coil made of round wire with a longitudinal coil axis. The adjacent instrument-receiving gaps between the turns of the coil may be dimensioned to accommodate the maximum depth of an instrument. The opposing support ends comprise an inboard side and an outboard side with a bottom edge, a top edge, and side edges. The inboard side of the opposing support ends may be flexibly fixed at the sides thereof in a substantially upright position to the respective terminal turn of the coil. The opposing support ends have a lower portion adapted for standing the instrument holding assembly on a surface and an upper portion adapted for use as a handle. The lower portion may define a slot defining diverging legs for stability on a surface. The upper portion may extend upright or the top edge may be angled outwardly at about 90 degrees or the like and may, optionally, terminate at the top edge with an upwardly extending lip for stacking purposes.

The opposing support ends may include a pair of opposing ring members that extend outwardly from or about each side edge of the opposing support ends. Each of the ring members may comprise a substantially C-shaped ring member adapted to receive one end of a restraint.

The opposing support ends may be a wire form or may be solid. The solid opposing support ends may include the opposing ring members or may include a substantially V-shaped notch in each side edge thereof for receiving one end of the restraint as hereinafter described.

The retracting member comprises an inverted substantially V-shaped perforated plate extending through the coil between opposing penultimate turns and along the bottom thereof. The plate is dimensioned to maintain the arms of the instrument as wide apart as possible to provide the best exposure to the hard to reach hinged area of the instrument and allow more penetration for washing the instruments.

The pair of restraints may be utilized to substantially prevent the one or more instruments from falling out of the instrument holding assembly during handling. The pair of restraints may be removably fastened over the sides of the coil between the opposing support ends. The stabilizing rod inside and on the bottom of the coil under the perforated retracting member extends between penultimate turns of the coil.

In another embodiment, the medical instrument holding assembly comprises a series of plates defining the instrument-receiving gaps and segregating the instruments. The plates may be positioned on edge in an upright position relative to the perforated retractor member. The plates may be any shape and may include a cutout (not shown) to fit over the perforated retractor member. The plates may be welded or the like to the perforated retractor member. The opposing support ends may be flexibly fixed to the terminal plates with the perforated retractor member and stabilizing rod extending between the penultimate plates Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 14 is an alternative environmental view of a plurality of loaded instrument holding assemblies positioned on sink dividers of a three deep sink.

DETAILED DESCRIPTION OF THE PREFERRED EMBODIMENTS

Figure 1:
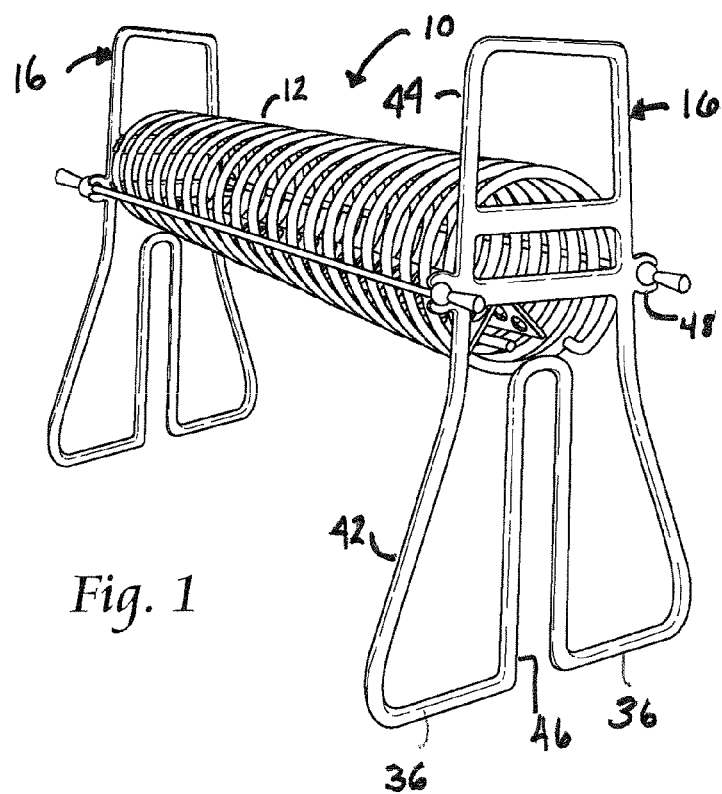
FIG. 1 is an elevational view of one side of an instrument holding assembly embodying the invention, illustrating a coil between wire form opposing support ends and defining instrument-receiving gaps, and a perforated plate and support rod extending through the coil with a restraint band extending across each side of the coil.
Figure 2:
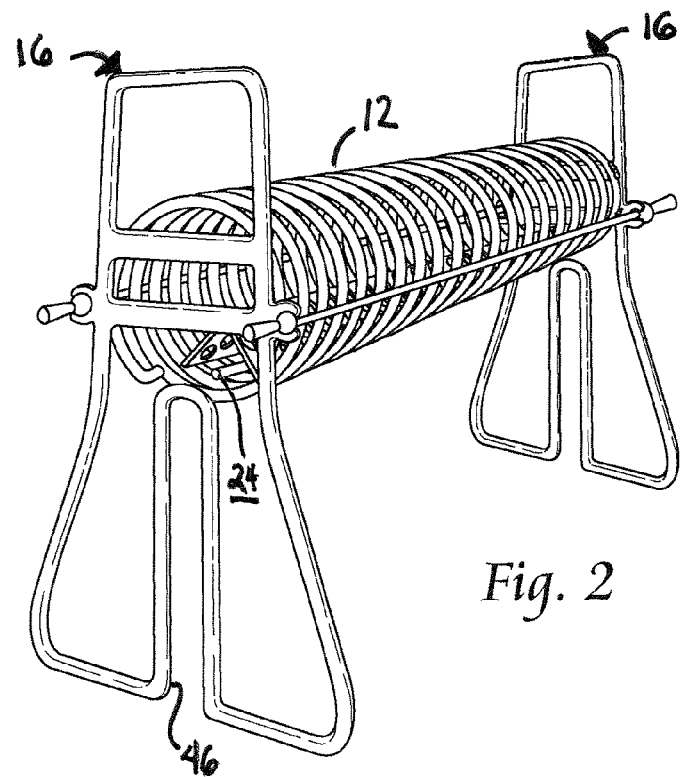
FIG. 2 is an elevational view of the opposite side of the instrument holding assembly of FIG. 1.
Figure 3:
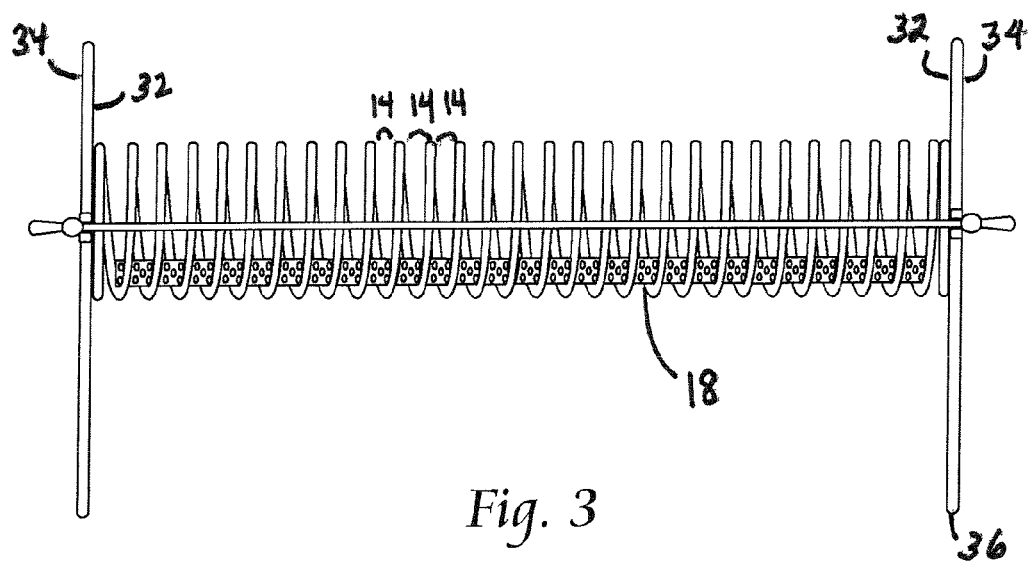
FIG. 3 is a side view of the instrument holding assembly of FIGS. 1-2.
Figure 4:
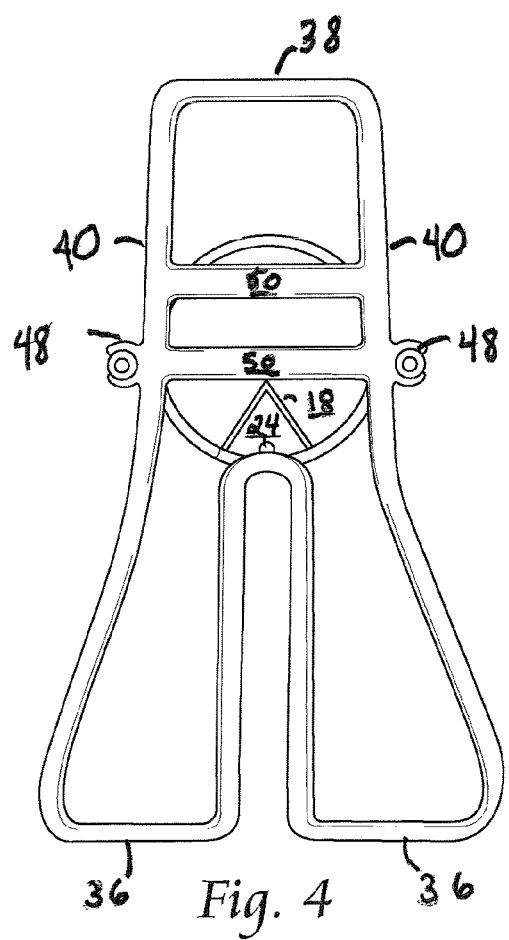
FIG. 4 is an end view of the instrument holding assembly of FIGS. 1-3.
Figure 5:
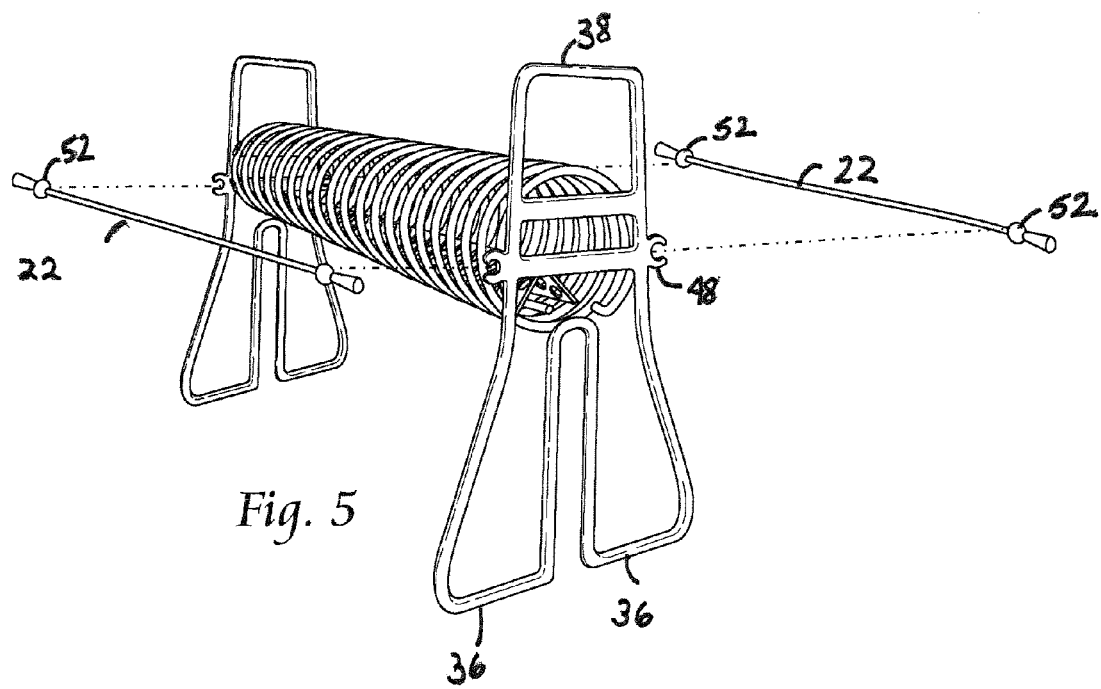
FIG. 5 is an assembly view of an instrument holding assembly of FIGS. 1-4, illustrating the placement of restraint bands into a pair of opposing ring members that extend sidewardly from each opposing support end.

As shown in the drawings for purposes of illustration, the present invention is concerned with a medical instrument holding assembly, generally designated in the accompanying drawings by the reference number 10. A medical instrument holding assembly 10 comprises, generally, a coil 12 defining adjacent medical instrument-receiving gaps 14, opposing support ends 16 for the coil, a perforated retractor member 18 adapted to maintain one or more medical instruments 20 in an open position in said medical instrument-receiving gaps, and a pair of restraints 22 adapted to restrain the one or more medical instruments therein. The medical instrument holding assembly may further comprise a stabilizing rod 24 for stabilizing the assembly.

In accordance with the present invention, and as illustrated with respect to a preferred embodiment, the medical instrument holding assembly 10 may be loaded with contaminated medical instruments and configured for removable placement in an instrument tray 26 for use in a washer sanitizer 28. The medical instrument holding assembly may also be used on sink dividers 30 or on other surfaces. The instrument holding assembly may be constructed of a metal that is easily cleaned, such as stainless steel or the like. There are approximately twenty different grades of stainless steel which fall into two predominant groups: Austenitic (i.e. 300 series) and martensitic (i.e. 400 series). Either group or a mixture thereof can be used for the instrument holding assembly. The material may be heat tempered or heat treated to withstand the high operating temperatures (typically 240° F.) within the washer sanitizer 28.

In a preferred embodiment as shown in FIGS. 1-9, the coil 12 may be a straight cylindrical coil made of round wire with a longitudinal coil axis. The coil comprises a series of concentric turns of substantially uniform dimension, preferably a continuous series of turns. The outer diameter of the wire may be in the range of about 0.050 inches to about 0.20 inches, preferably about 0.125 inches to impart rigidity to the coil. The wire for the coil may be rectangular, round, square or special-section, with round being the most adaptable. The outside diameter of the coil may be in the range of about 1.00 inches to about 3.0 inches, preferably about two inches. The free length of the coil measures slightly less than the width of the instrument tray 26. Current instrument trays are available in widths of 10.5 inches and 8.5 inches. The free length for the coils may therefore be about 10⅛ inches long and about 8⅛ inches long to respectively fit securely within instrument trays of these widths. For instrument trays of other dimensions, the length of the coil may be adjusted accordingly. A suitable coil is available from Arizona Spring & Coil, Chandler, Ariz.

The adjacent instrument-receiving gaps 14 between the turns of the coil may be dimensioned to accommodate the maximum depth of an instrument (i.e. the thickest part of the instrument). While not intended to be limiting, the distance (d) between adjacent turns may be about ⅛ inch to about 1 inch, preferably greater than ¼ inches. The number of coils less one corresponds to the maximum number of instruments that may be loaded into the instrument holding assembly.

The opposing support ends 16 comprise an inboard side 32 and an outboard side 34 with a bottom edge 36, a top edge 40, and side edges 42. The inboard side 32 of the opposing support ends 16 may be flexibly fixed at the sides thereof in a substantially upright position to the respective terminal turn of the coil. The opposing support ends 16 have a substantially triangular-shaped lower portion 42 adapted for standing the instrument holding assembly on a surface and a substantially rectangular-shaped upper portion 44 adapted for use as a handle. The lower portion includes the bottom edge 36. The lower portion may define a slot 46 between and substantially parallel to the side edges defining diverging legs for mounting on a sink divider 30 as hereinafter described. It is to be appreciated that the slot may be eliminated if the instrument holding assembly is not to be used on a sink divider.

Figure 8:
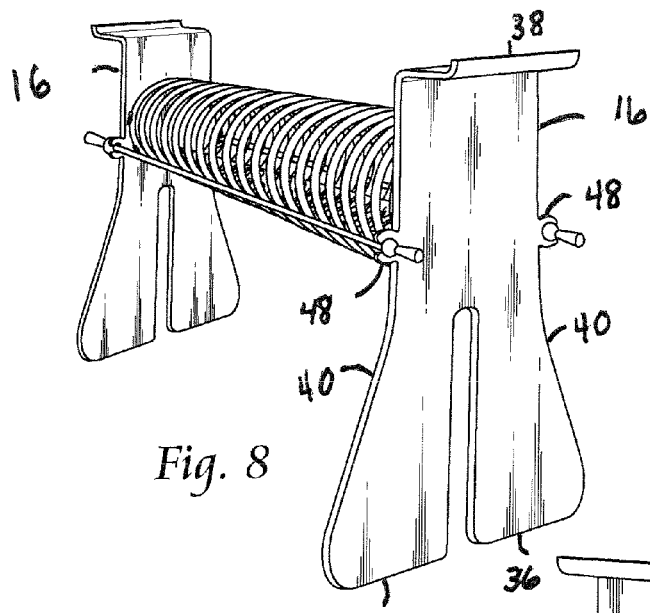
FIG. 8 is a perspective view of the instrument holding assembly, illustrating solid opposing support ends.
Figure 9:
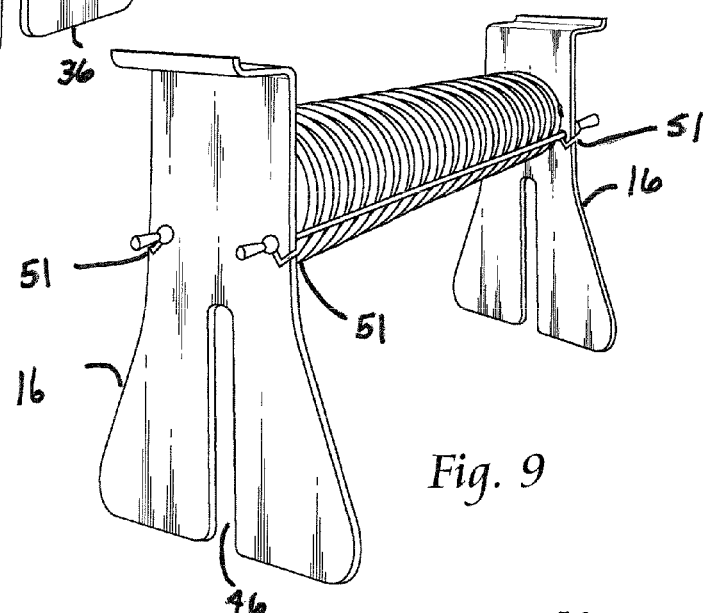
FIG. 9 is an elevational view of the opposite side of the instrument holding assembly of FIG. 8.
Figure 10:
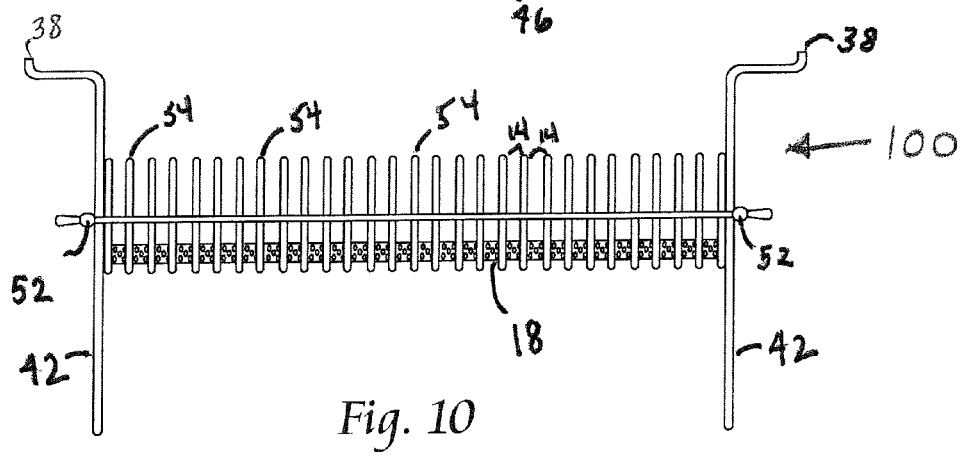
FIG. 10 is another embodiment of an instrument holding assembly, illustrating a series of plates defining instrument-receiving gaps between opposing support ends.
Figure 11:
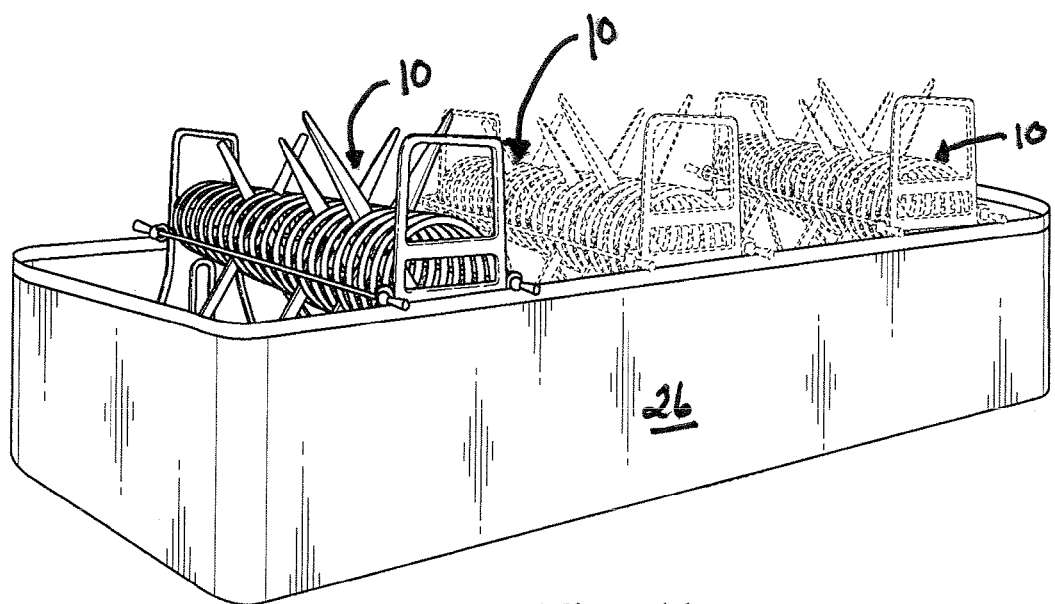
FIG. 11 is a perspective environmental view of a plurality of loaded instrument holding assemblies inside an instrument tray, illustrating the opposing support ends within (inboard) the instrument tray.

The upper portion may extend upright as shown in FIGS. 1-7. Alternatively, the top edge may be angled outwardly at about 90 degrees or the like and may, optionally, terminate at the top edge 42 with an upwardly extending lip as shown in FIGS. 8-10. The lip enables stacking of the assemblies (not shown). The total height of the opposing support ends may be slightly less than the known height between racks of the washer-sanitizer so as to not interfere with placement of the loaded instrument tray therein (See FIG. 13).

The opposing support ends may include a pair of opposing ring members 48 that extend outwardly from or about each side edge 40 of the opposing support ends. Each of the ring members may comprise a substantially C-shaped ring member adapted to receive one end of a restraint 22 as hereinafter described.

As shown in FIGS. 1-7 and 11-13, the opposing support ends may be a wire form manufactured of stiff wire with an outer diameter ranging from about 0.090 inches to about 2.0 inches, preferably 0.155 inches. The inboard side 32 of the opposing support ends 16 may include one or more horizontal cross bars 50 in substantially the middle thereof for purposes as hereinafter described.

As shown in FIG. 8, the opposing support ends 16 may be solid. The solid opposing support ends may be stamped or cut out of a sheet of stainless steel or the like. The solid opposing support ends may include the opposing ring members 48 (FIG. 8) or may include a substantially V-shaped notch 51 (FIG. 9) in each side edge thereof for receiving one end of the restraint 22 as hereinafter described. While the solid support ends are shown as having an angled upper portion, it is to be appreciated that substantial benefit may be derived from the wire form support ends having an upper portion that is similarly angled at the top edge.

The perforated retracting member 18 maintains the one or more instruments in an open and vertical position in each instrument-receiving gap defined between the turns of the coil. In a preferred embodiment, the retracting member 18 comprises an inverted substantially V-shaped perforated plate extending through the coil between opposing penultimate turns and along the bottom thereof. The pitch of the perforated plate (i.e. the highest point) may be substantially centered between the sides of the coil. The perforated plate may be mounted on the inside bottom of the coil. The plate is dimensioned to maintain the arms of the instrument as wide apart as possible to provide the best exposure to the hard to reach hinged area of the instrument and allow more penetration for washing the instruments. The plate is substantially rigid to provide stability. The perforations allow the cleaning solutions and lubricants to penetrate into the open hinged area. While a substantially V-shaped perforated plate is shown as the preferred retractor member, it is to be appreciated that substantial benefit may be achieved by the use of a perforated retractor member other than the substantially V-shaped plate, for example, by a perforated strip, bar, or the like under the hinged area to maintain the arms of the instrument in a spread apart position.

The pair of restraints 22 may be utilized to substantially prevent the one or more instruments from falling out of the instrument holding assembly 10 during handling. The restraints may be removable and replaceable. The restraints 22 may be bands with a ball 52 near each end. The restraints may preferably be formed of a pliable elastic tubing material that will not damage the instruments that come into contact with the restraints while the instruments are loaded in the instrument holding assembly 10. Suitable materials include nylon or the like. Referring to FIGS. 1-3 and 5-14, the bands may be removably fastened over the sides of the coil between the opposing support ends with each ball 52 secured on the outboard side 34 of the opposing support ends to hold the restraint bands in place. The bands may be received in the substantially C-shaped ring members 48 or the substantially V-shaped notches 51 in the opposing support ends. While bands removable from opposing ring members and the substantially V-shaped notches have been described, substantial benefit may be derived from bands that are removable from one end only.

The stabilizing rod 24 inside and on the bottom of the coil 12 under the perforated retracting member 18 extends between penultimate turns of the coil which permits the opposing support ends to be securely fastened against the sidewalls of the instrument tray in either an inboard (FIG. 11) or an outboard position (FIG. 12) as hereinafter described. The stabilizing rod 24 also substantially prevents the instrument holding assembly from swaying or sagging under the weight of a plurality of instruments and provides stability to the retracting member.

In another embodiment as shown in FIG. 10, the medical instrument holding assembly 100 comprises a series of plates 54 defining the instrument-receiving gaps. The series of plates segregate or separate the medical instruments when the assembly is loaded. The plates may be positioned on edge in an upright position relative to the perforated retractor member. The plates may be any shape and may include a cutout (not shown) to fit over the perforated retractor member. The plates may be welded or the like to the perforated retractor member. The opposing support ends 16 may be flexibly fixed to the terminal plates with the perforated retractor member 18 and stabilizing rod 24 extending between the penultimate plates in the same manner as described above.

The instrument holding assembly 10 and 100 may be used to hold medical instruments 20, particularly surgical instruments. Many surgical instruments comprise two arms which are joined at a pivot and comprise handles at their proximal end i.e. the handles are hinged at the pivot point. A box lock comprises the preferred hinge. Ring handles are common handles for surgical instruments. Typical surgical instruments that may be cleaned in the instrument holding assembly include scissors, criles, kochers, kellys, mosquitos, tovel clamps, needle holders, or the like. This is not an exhaustive list of the medical or surgical instruments that may be cleaned while loaded in the instrument holding assembly.

Figure 6:
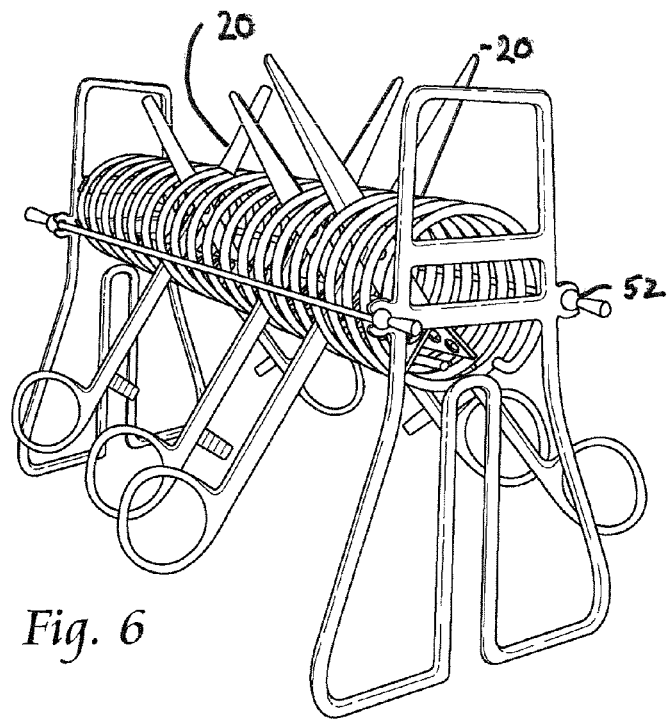
FIG. 6 is a perspective environmental view of a loaded instrument holding assembly, illustrating a plurality of opened exemplary instruments in the instrument-receiving gaps between adjacent turns of the coil.
Figure 7:
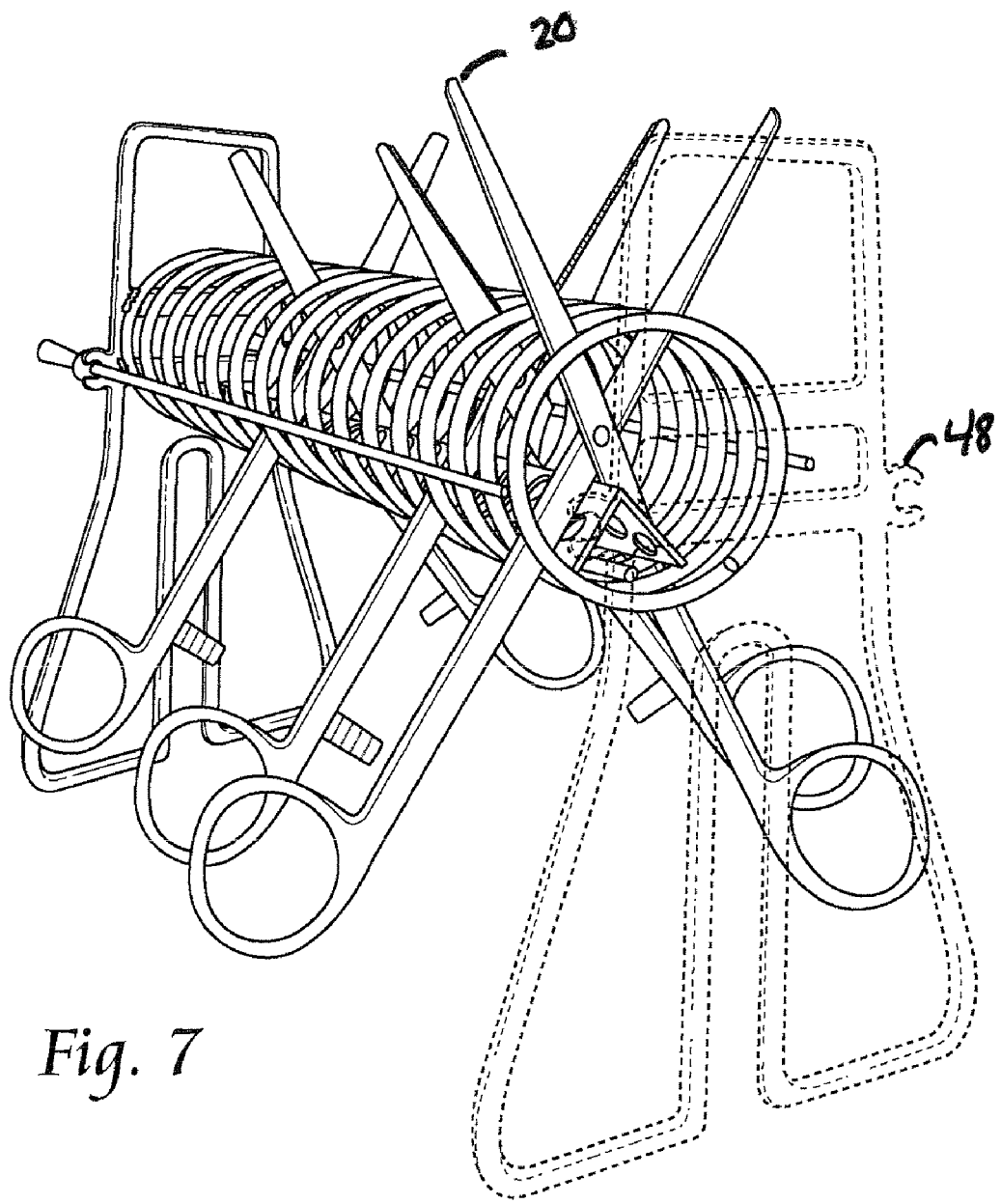
FIG. 7 is another perspective environmental view similar to FIG. 6 with one of the opposing support ends shown in dotted lines, illustrating the perforated plate inside the coil maintaining the exemplary instruments in an open position.

In use, the contaminated instruments are unlocked if necessary and opened to expose the hinged area. The instrument may be loaded into the instrument holding assembly 10 and 100 by placing the opened instrument into one of the instrument-receiving gaps 14. Each instrument may have a space of its own separated by a turn of the coil or a plate 54 in order to substantially prevent contact between instruments thus minimizing damage thereto. The instruments may be loaded vertically into the instrument holding assembly with the handles pointing down and the tips pointed upwardly as shown in FIG. 6. The pitch of the perforated plate 18 fits within the instrument hinged area on the handle end of the instruments (See FIG. 7) and thus maintains the instrument in an open position exposing the hinged area on the tip or working end of the instruments and permitting better cleaning thereof. The pair of restraint bands 22 is then removably fastened into the pair of opposing ring members 48 or substantially V-shaped notches 51.

Figure 12:
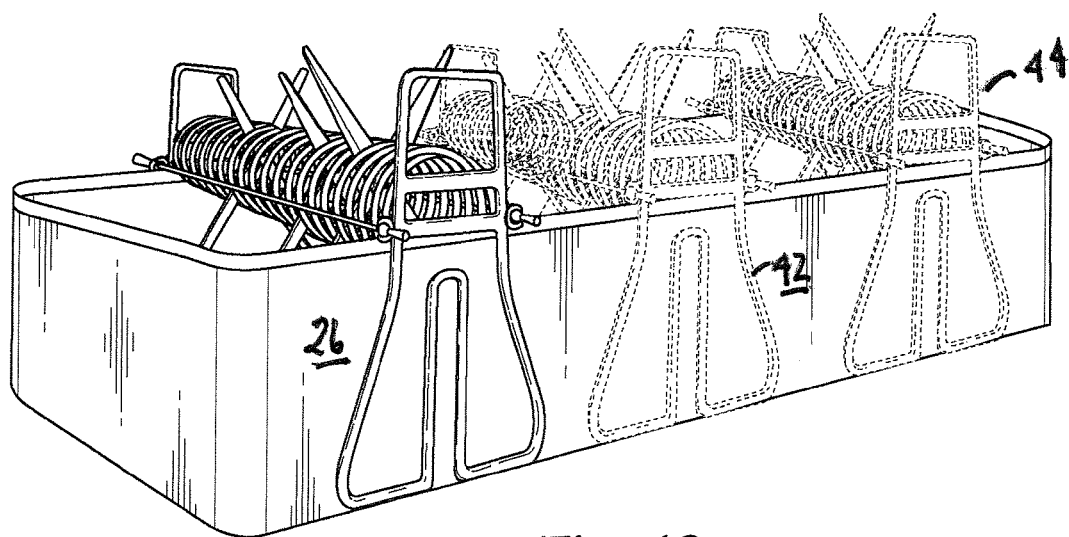
FIG. 12 is an alternative perspective environmental view similar to FIG. 11, illustrating the manner in which the support ends may be removably fixed over the sides outboard of the instrument tray.

As shown in FIGS. 8 and 9, the instrument holding assembly may be used in the instrument tray 26. The typical instrument tray is substantially rectangular, typically has a perforated bottom (not shown) to permit drainage, four sidewalls 26a having a height representing the depth of the instrument tray, and an open top. The instrument tray can typically accommodate a plurality of instrument holding assemblies 10 and 110. The instrument holding assembly(ies) may be positioned in the instrument tray across the width of the tray to accommodate the footprint of a loaded instrument holding assembly i.e. to allow for clearance with the handles spread apart exposing the hinged area with the lower portion 32 of the support ends positioned against opposing sidewalls 26a within the instrument tray (FIG. 11) and the bottom edge 40 adapted for placement on or near the bottom of the instrument tray. The one or more horizontal cross bars 50 help securely level the instrument holding assembly in the instrument tray. A typical height from the bottom of a tray to the top of the handles is 5¼ inches. Alternatively, the inboard side 36 of the opposing support ends may be removably fixed against the outside of the instrument tray sidewalls 26a (FIG. 12). Although the instrument holding assemblies are shown as separate from the instrument tray, it is to be appreciated that substantial benefit may be derived from instrument holding assemblies that are integral with the instrument trays.

Figure 13:
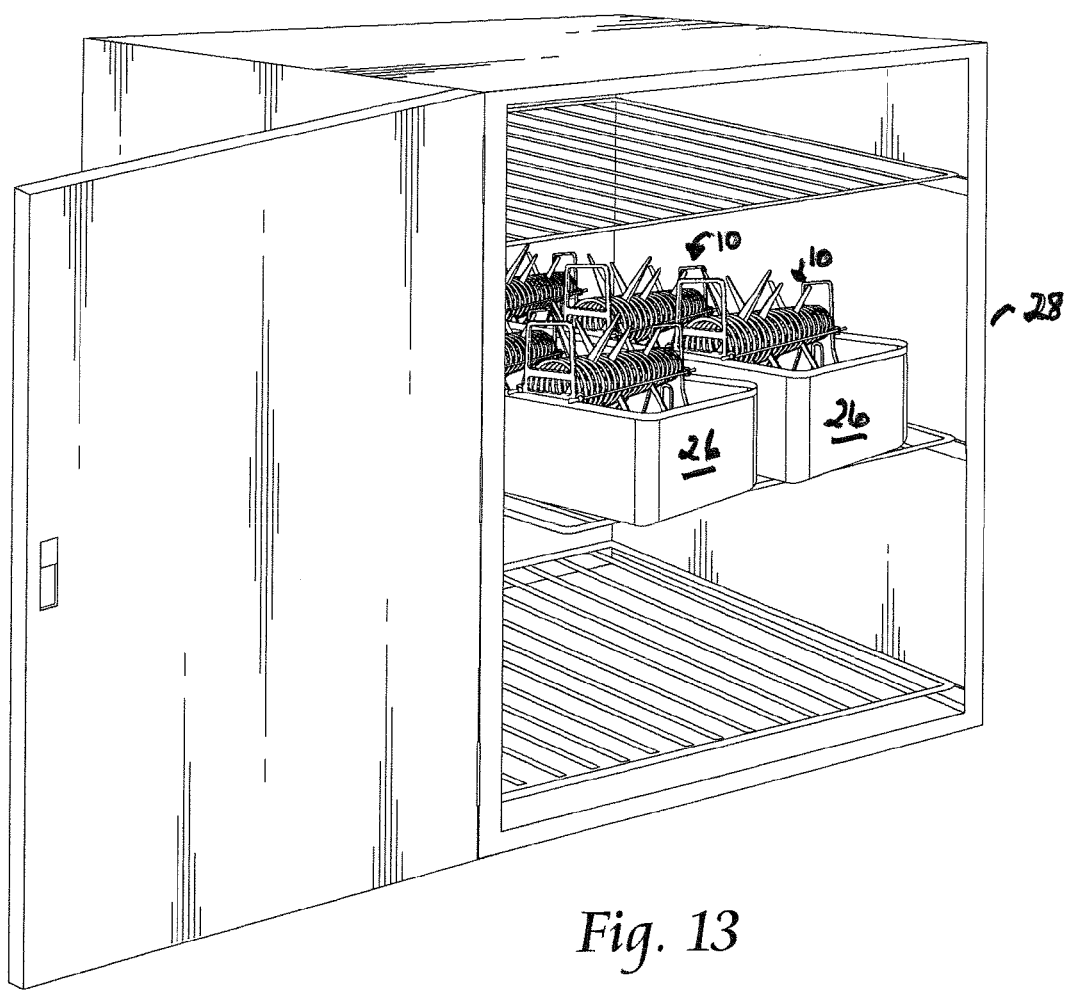
FIG. 13 is an exemplary environmental view, illustrating a plurality of loaded instrument holding assemblies inside the instrument tray and its positioning within a representative washer-sanitizer.

The loaded instrument tray may be placed in the washer sanitizer 28 (See FIG. 13) for mechanical cleaning of the instruments by impingement from sprayers (not shown) and, optionally, for lubrication. The washer sanitizer typically includes a plurality of racks and is sized to accommodate a plurality of instrument trays on each rack as shown in FIG. 13. A sprayer (not shown) is typically positioned over each rack in the washer sanitizer 28 and above the upwardly opened hinged area of the instruments thus providing for optimal exposure of the hinged area (typically on the working end of the instrument) to impingement from the sprayer overhead.

The instrument holding assembly may also be removably mounted on sink divider(s) 30 (FIG. 14) in a three deep sink configuration 56 or the like for help in manual cleaning of the instruments. When used in this manner, the sink divider is received into the slot 46 in the support ends. The instrument holding assembly may also be used on a counter (not shown) or table (not shown) to organize instruments as needed.

After cleaning, the decontaminated (and optionally, lubricated) instruments may be easily and hygienically removed from the instrument holding assembly 10 and 100 by removing at least one end of both restraint bands 22 from the ring members 48 and gripping the instrument handles to withdraw the instrument away from the instrument holding assembly. The instrument holding assembly may also be emptied of a plurality of instruments at one time by removing at least one end of both restraint bands and gently permitting the instruments to fall away from the instrument holding assembly into a receptacle or the like.

From the foregoing, it is to be appreciated that the instrument holding assembly of the present invention provides maximum stabilization of the medical instruments during pre-sterilization cleaning and/or lubrication thus preserving their value and usefulness. In addition, the instrument holding assembly permits better cleaning of the surgical instruments, particularly in the hard-to-clean hinged areas. The instrument holding assembly is quite easy to use by personnel to clean many surgical instruments at one time.

Although a particular embodiment of the invention has been described in detail for purposes of illustration, various modifications may be made without departing from the spirit and scope of the invention. Accordingly, the invention is not to be limited, except as by the appended claims.

We claim:

1. An instrument holding assembly for holding one or more medical instruments during pre-sterilization cleaning, comprising in combination:
    a coil defining medical instrument-receiving gaps between adjacent turns of said coil and opposing support ends mounted in a substantially upright position at each end of said coil;
    an inverted V-shaped plate positioned in an interior of the coil and attached to and running along a bottom section of the longitudinal axis of the coil and between penultimate turns of the coil, an apex of the V-shaped plate is substantially centered in the interior of the coil and directed toward a top of the coil, wherein a hinged section of the one or more medical instruments is positioned on top of the apex to hold the one or more medical instruments in an upright position and above a surface on which the instrument holding assembly is positioned; and
    a plurality of perforations formed though the inverted V-shaped plate, the perforations allowing cleaning solutions and lubricants to flow through the inverted V-shaped plate to penetrate instruments positioned in the holding assembly.

2. The instrument holding assembly of claim 1, further comprising:
    restraint means adapted to restrain the one or more medical instruments in the instrument holding assembly, the restraint means being a pair of rod members, an individual rod member detachable connected to opposing side surfaces of the coil to keep the at last one medical instruments in an upright position.

3. The instrument holding assembly of claim 2, wherein the opposing support ends comprise a lower portion adapted for positioning the instrument holding assembly on a surface and an upper portion adapted as a handle.

4. The instrument holding assembly of claim 3, wherein the upper portion is angled at about 90 degrees and terminates in an upwardly extending lip.

5. The instrument holding assembly of claim 3, wherein the opposing support ends are solid and the ends of the restraint means are each received in a substantially V-shaped notch in the side edges of the opposing support ends.

6. An instrument holding assembly for holding one or more surgical instruments during pre-sterilization cleaning, comprising:
    a coil defining surgical instrument-receiving gaps between adjacent turns of said coil;
    opposing support ends for said coil comprising a lower portion and an upper handle portion;
    an inverted V-shaped plate positioned in an interior of the coil and attached to a bottom section of the longitudinal axis of the coil and between penultimate turns of the coil, an apex of the V-shaped plate is substantially centered in the interior of the coil and directed toward a top of the coil, wherein a hinged section of the one or more medical instruments is positioned on top of the apex to hold the one or more medical instruments in an upright position and above a surface on which the instrument holding assembly is positioned;
    a plurality of perforations formed though the inverted V-shaped plate, the perforations allowing cleaning solutions and lubricants to flow through the inverted V-shaped plate to penetrate instruments positioned in the holding assembly; and
    a pair of restraint bands removably fastened over the sides of the coil between opposing support ends.

7. The instrument holding assembly of claim 6, further comprising a stabilizing rod positioned inside and on the bottom of the coil under the V-shaped plate and extending between penultimate turns of the coil which permits opposing support ends to be securely fastened against sidewalls of an instrument tray, the stabilizing rod preventing the instrument holding assembly from one of swaying or sagging under a weight of a plurality of instruments.

8. The instrument holding assembly of claim 6, wherein the opposing support ends include ring members extending sidewardly there from for removable fastening of said pair of restraint bands over each side of said coil between opposing support ends.

9. The instrument holding assembly of claim 6, wherein the opposing support ends include a substantially V-shaped notch at each side edge thereof for removably fastening of said pair of restraint bands between opposing support ends.

10. The instrument holding assembly of claim 6, wherein the lower portion of the opposing support ends comprises a pair of diverging legs for supporting the instrument holding assembly on a surface.

11. The instrument holding assembly of claim 6, wherein the opposing support ends are flexibly fixed in an upright position at each end of the coil.

12. The instrument holding assembly of claim 11, wherein the upper handle portion extends outwardly and terminates in an upwardly extending lip adapted for stacking said instrument holding assemblies.

* * * * *